(12) United States Patent
Pfutzner et al.

(10) Patent No.: US 8,990,020 B2
(45) Date of Patent: Mar. 24, 2015

(54) METHOD AND APPARATUS FOR MEASURING THE VERTICAL SEPARATION OF TWO STATIONS IN A BOREHOLE

(75) Inventors: Harold Pfutzner, Richmond, TX (US); Peter D. Wraight, Skillman, NJ (US)

(73) Assignee: Schlumberger Technology Corporation, Sugar Land, TX (US)

( * ) Notice: Subject to any disclaimer, the term of this patent is extended or adjusted under 35 U.S.C. 154(b) by 656 days.

(21) Appl. No.: 12/698,687

(22) Filed: Feb. 2, 2010

(65) Prior Publication Data

US 2011/0191027 A1 Aug. 4, 2011

(51) Int. Cl.
| | |
|---|---|
| *G01V 1/40* | (2006.01) |
| *G01V 7/06* | (2006.01) |
| *E21B 49/08* | (2006.01) |
| *E21B 47/10* | (2012.01) |
| *E21B 47/00* | (2012.01) |
| *G01N 9/36* | (2006.01) |
| *G01V 1/50* | (2006.01) |

(52) U.S. Cl.
CPC . *G01V 7/06* (2013.01); *E21B 49/08* (2013.01); *E21B 47/00* (2013.01); *E21B 47/10* (2013.01); *G01N 9/36* (2013.01); *G01V 1/50* (2013.01)
USPC ...... 702/6; 702/8; 702/12; 702/100; 702/137; 250/254; 250/269.1; 250/269.3; 73/32 A; 73/32 R

(58) Field of Classification Search
USPC ......... 702/6, 7, 8, 11, 12, 16, 40, 50, 98, 100, 702/137, 134, 138, 166, 172
See application file for complete search history.

(56) References Cited

U.S. PATENT DOCUMENTS

| | | | | |
|---|---|---|---|---|
| 4,475,386 | A | * | 10/1984 | Fitch et al. ................... 73/382 R |
| 4,596,139 | A | | 6/1986 | Gournay |
| 4,607,694 | A | | 8/1986 | Sah |
| 5,970,787 | A | | 10/1999 | Wignall |
| 6,097,786 | A | | 8/2000 | Groves et al. |
| 6,189,383 | B1 | * | 2/2001 | Tello et al. ....................... 73/589 |
| 6,206,108 | B1 | * | 3/2001 | MacDonald et al. ........... 175/24 |
| 7,075,062 | B2 | | 7/2006 | Chen et al. |
| 7,377,169 | B2 | | 5/2008 | Myers et al. |
| 2002/0121371 | A1 | | 9/2002 | Moake et al. |
| 2007/0274443 | A1 | * | 11/2007 | Groves et al. .................... 378/54 |
| 2009/0164187 | A1 | | 6/2009 | Habashy et al. |

OTHER PUBLICATIONS

J.V. Popta et al., "Use of Borehole Gravimetry for Reservoir Characterisation and Fluid Saturation Monitoring," SPE 20896, pp. 151-160 (Oct. 1990).
International Search Report and the Written Opinion for International Application No. PCT/US2011/022688 dated Jul. 26, 2014.

* cited by examiner

*Primary Examiner* — Sujoy Kundu
*Assistant Examiner* — Paul D Lee
(74) *Attorney, Agent, or Firm* — Cathy Hewitt

(57) ABSTRACT

A system and method for use in a downhole tool having a fluid density measurement device positioned therein are provided. In one example, the method includes deploying the downhole tool at a first station in a borehole. The downhole tool is moved from the first station to a second station in the borehole. A plurality of fluid density values of fluid within the borehole between the first and second stations are measured using the fluid density measurement device in the downhole tool. The plurality of fluid density values may represent a continuous log of fluid densities between the first and second stations.

13 Claims, 9 Drawing Sheets

METHOD AND APPARATUS FOR MEASURING THE VERTICAL SEPARATION OF TWO STATIONS IN A BOREHOLE

BACKGROUND

Exploration for underground resources such as hydrocarbons includes the evaluation of reservoirs to determine the presence and/or movement of fluids such as oil, gas, and water. One method for such an evaluation includes the use of measurements obtained using a downhole tool. For example, gravity measurements may be used to map out the vertical distribution of oil and gas in a borehole by enabling the calculation of the bulk density of an area adjacent to the downhole tool based in part on relatively minute gravity changes between different positions of the borehole.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1A:
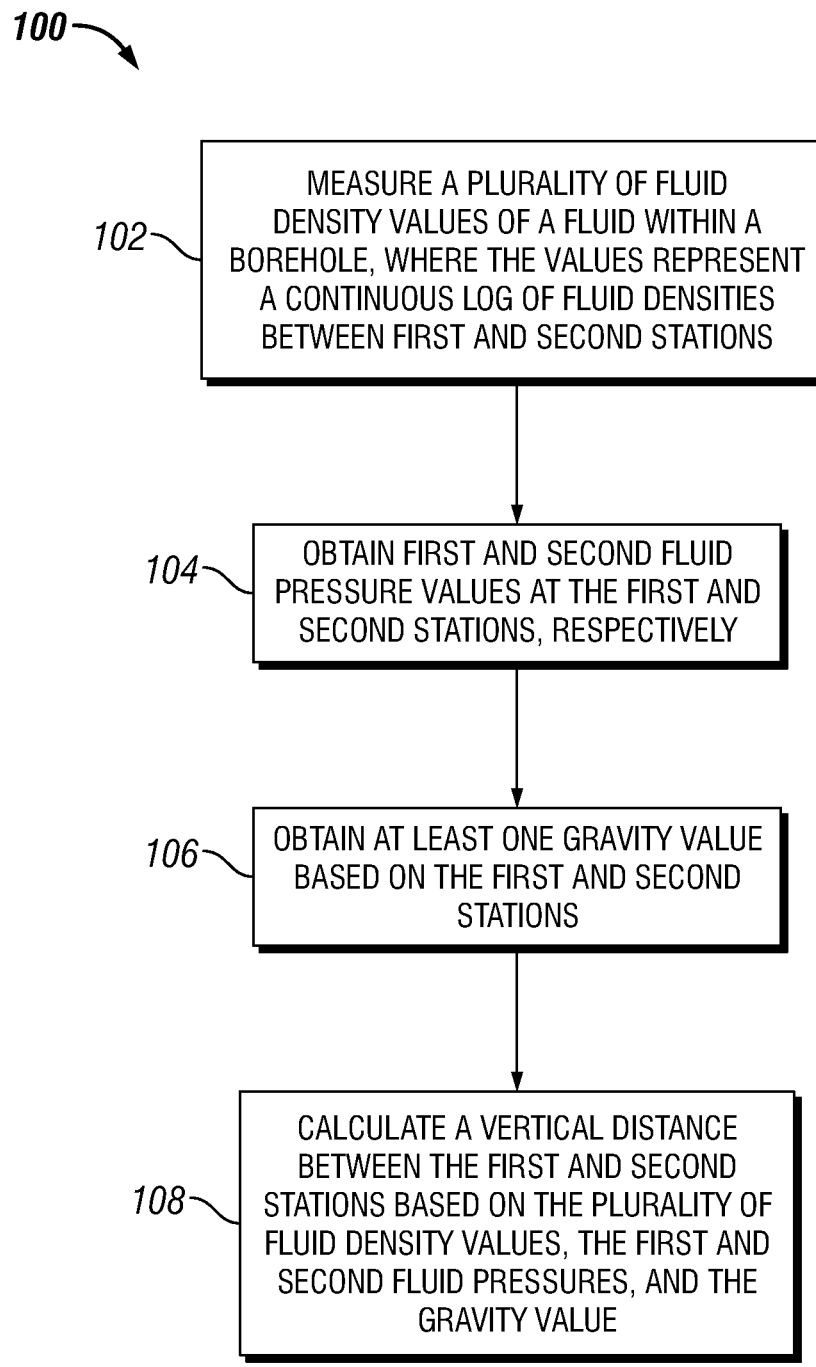
FIG. 1A is a flow chart diagram of at least a portion of a method according to one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Differential measurements of gravitational acceleration (henceforth referred to as gravity) obtained in a borehole are used for calculating the bulk density of a formation. The differential aspect of the measurement compensates for the continuous and approximately linear drift of the gravity sensor output. For example, two or three measurements may be taken in rapid succession and in close proximity to each other. The first measurement may be taken at some position in the borehole. A second measurement may be taken some vertical distance $\Delta z$ above or below the first measurement. A third measurement may be taken at the same position as the first measurement. The first two measurements are subtracted and a drift correction applied. The drift correction may be determined from the difference between the first and third measurements and the timing of all three measurements.

In addition to providing a technique for drift correction, the differential measurement may be useful for calculating the average bulk density of a theoretical, horizontal, infinite slab located between the two measurement positions having vertical coordinates at z and z−$\Delta z$. The equation for bulk density, $\rho$, as measured via borehole gravimetry is:

$$\rho = K_1 - K_2\left(\frac{\Delta g}{\Delta z}\right) \qquad \text{Equation 1}$$

where $\Delta g$ is the difference between two gravity measurements taken at two different vertical stations and $\Delta z$ is the measured vertical separation (excluding any horizontal component) between the two stations. $K_1$ is 3.701 g/cm$^3$ and $K_2$ is 12 (g/cm$^3$)(m/mGal). In this formulation, $\rho$ is in units of g/cm$^3$, $\Delta g$ is in mGal, and $\Delta z$ is in m.

As illustrated in Equation 1, the bulk density is dependent upon both gravity and vertical distance measurements. Accordingly, the precision of the bulk density calculation depends on the precision of these two measurements.

A simple method for measuring vertical distance is to use an odometer at the surface to record the amount of wireline cable spooled on or off of a winch drum as the downhole tool is moved from a first logging position for the first measurement to a second logging position for the second measurement and then back to the first logging position for the third measurement. This measurement can be adjusted by cosine ($\theta$) in the case of a deviated well in order to obtain the true vertical depth, where $\theta$ is the angle of the well with respect to the vertical. However, this method is limited by the precision of the odometer or other device measuring the cable movement and by stretch in the cable. The measurement of $\Delta z$ may also be affected by error in the measurement of $\theta$, which is usually measured with an inclinometer in the tool or obtained from the drilling records.

For a short $\Delta z$ of a few meters, a separate internal conveyance mechanism (e.g., an elevator or shuttle mechanical device) with a very precisely known travel distance may be used. The conveyance mechanism is inside the tool's pressure housing and has a gravimeter rigidly connected to it. One example of such a borehole gravity tool was built by LaCoste & Romberg circa 1980 for the U.S. Geological Survey (USGS) and Atlantic-Richfield Company (ARCO), and has a conveyance mechanism with a travel distance of 2.5 meters. Using an internal conveyance mechanism may provide a measurement precision for $\Delta z$ of approximately one to three millimeters out of 2.5 meters. The main disadvantage with the use of such an internal conveyance mechanism is that it is limited to a relatively short $\Delta z$. It also adds to the length and cost of the downhole tool in which it is placed.

With many downhole logging tools, the depth of investigation (i.e., the sensitivity of the measurement to a formation that is some distance in the horizontal plane away from a vertical borehole) is related to and of the same magnitude as the source to receiver spacing. For compensated logging tools based on resistivity or gamma-gamma density, this is the spacing between the source and the primary or compensating detector and for the gravimeter it is the spacing, $\Delta z$, between the two measurements. For some applications of borehole gravimetry, such as water flood or gas cap monitoring in a hydrocarbon reservoir, it may be desirable to sense changes in gravity at relatively large distances (e.g., tens to hundreds of meters) from the borehole. In these cases, it may not be practical to have a conveyance mechanism with the necessary travel length inside a downhole tool.

For scenarios dealing with a larger $\Delta z$, various conventional methods known in the art may be used. For example, in cased holes, it may be possible to locate the casing collars by their increased magnetic permeability using a casing collar locator (CCL) tool. From the known length of the casing sections, $\Delta z$ may be obtained when the gravity measurements are taken at the casing collars. However, this method may be limited in precision by the measurement of the lengths of casing sections and the assumed overlap of casing joints, by casing sections stretching or compressing unevenly over time in the presence of subsidence or tectonic forces, and/or by the length of the casing collar itself, which may be ten to twenty centimeters long and may not give a repeatable indication of its position on the CCL log. The requirement in this method to locate the gravity measurement at the casing collar is severely limiting and may reduce the value of the measurement.

An alternative to the use of a CCL tool for determining $\Delta z$ includes the use of gamma-ray logs. A position in an open or cased well may be precisely located (e.g., within five to fifteen centimeters) by a gamma-ray log, but should still be correlated to some other measurement of length, such as the winch-mounted odometer described previously. This correlation may introduce imprecision into the calculations due to the limitations of such odometers.

One approach that may be used to solve the issues described with the preceding measurement methods uses the difference in pressure at the two measurement stations of a fluid column present within the borehole. Although this method may be limited by such factors as the accuracy and precision of the pressure measurement itself and from variations in the fluid density that may exist between the two measurement stations, this method may not be sensitive to inclination and changes in inclination along the well path. In other words, this method may be sensitive to the true vertical separation $\Delta z$ that is needed for the bulk density measurement and may be used for large values of $\Delta z$ and for smaller values of $\Delta z$ to the extent allowed by the pressure measurement's accuracy and precision.

As is known, the pressure difference $\Delta P$ between the top and bottom of a fluid column is related to the height of the fluid column $\Delta h$ through the equation:

$$\Delta P = \rho g \Delta h \qquad \text{Equation 2}$$

This principle is the basis of the mercury-filled barometer and also applies in a fluid-filled borehole. However, instead of measuring atmospheric pressure, the vertical distance between two points in the borehole is determined by calculating the difference of pressure measurements taken at those two points according to the equation:

$$\Delta z = \frac{\Delta P}{\rho_f \cdot g} \qquad \text{Equation 3}$$

In Equation 3, $\Delta P$ equals the pressure difference between two stations, $\rho_f$ is the borehole fluid density, and g is the calculated average acceleration due to gravity for that vertical depth. In the present example, mixed units are used with $\Delta P$ in kPa, $\rho_f$ in g/cm$^3$, g in m/s$^2$ and $\Delta z$ in m.

It is noted with respect to Equation 3 that $\Delta z$ is always the true vertical distance between the two points, regardless of the shape or path of the borehole. More specifically, boreholes are not perfectly vertical or straight and in many cases may be deliberately deviated as much as 90° from vertical. In horizontal boreholes, it is common for the borehole to go uphill (i.e., have a deviation greater than 90°) in some sections. However, for any path of a deviated borehole, Equation 3 provides the correct vertical distance.

The fluid in a borehole often has an inhomogeneous fluid density. For example, boreholes may contain mixtures of fresh water, salt water, oil of various densities, gas, and drilling fluids. These different fluids may become segregated over the length of the borehole, resulting in an inhomogeneous fluid density. For a large $\Delta z$, this lack of uniformity may cause significant errors in the measurement of $\Delta z$. Accordingly, as will be described below in greater detail, it may be desirable to continuously measure the fluid density over the interval spanned by $\Delta z$ (e.g., the distance between two measurement stations).

For large separations of $\Delta z$ where the fluid density may not be homogeneous, it may be desirable to sum over the interval using a continuous log of $\rho_f$. In the case of a continuous log, $\rho_f$ becomes the average fluid density over the length $\Delta z$ as illustrated by $$\langle \rho_f \rangle = \frac{2 \sum_{i=1}^{n} \rho_{f_i} d\cos(\theta_i) - [\rho_{f1} d\cos(\theta_1) + \rho_{fn} d\cos(\theta_n)]}{(n-1)\left\{2 \sum_{i=1}^{n} d\cos(\theta_i) - [d\cos(\theta_1) + d\cos(\theta_n)]\right\}} \qquad \text{Equation 4}$$

where i is an index for the logged fluid density and inclination data points that span the interval of the two station measurements, d is the fixed logging interval as recorded by the odometer (e.g., six inches), $\rho_{f_i}$ is the fluid density at the i$^{th}$ depth, and $\theta_i$ is the well inclination at the i$^{th}$ depth. In Equation 4, d is common to all terms and may be factored out, resulting in $$\langle \rho_f \rangle = \frac{2 \sum_{i=1}^{n} \rho_{f_i} \cos(\theta_i) - [\rho_{f1} \cos(\theta_1) + \rho_{fn} \cos(\theta_n)]}{(n-1)\left\{2 \sum_{i=1}^{n} \cos(\theta_i) - [\cos(\theta_1) + \cos(\theta_n)]\right\}} \qquad \text{Equation 5}$$

Accordingly, accurate calculation of the vertical distance between two stations using an average fluid density may provide increased accuracy in, for example, calculations for bulk density. After using Equation 3 to calculate a value for $\Delta z$, the bulk density $\rho$ as measured via borehole gravimetry may be calculated as described previously using Equation 1.

The following disclosure provides methods and tools for increasing the accuracy of fluid density measurements between two stations in a borehole and for calculating the vertical distance between two stations based at least partially on those measurements.

FIG. 1A is a flow-chart diagram of at least a portion of a method 100 according to one or more aspects of the present disclosure. The method 100 may be or comprise a process for measuring fluid density in a borehole. These fluid density measurements may then be used to obtain an accurate vertical distance from a differential pressure measurement in the presence of varying fluid density.

In step 102, measurement instrument(s) within a downhole tool positioned within the borehole are used to measure a plurality of fluid density values of the fluid within the borehole. The measurements may be made while the tool is moving and/or when the tool is stopped. The values may represent a continuous log of fluid densities between first and second stations within the borehole. It is understood that the term "continuous" as used in the present disclosure is not limited to measurements that occur without any interruption whatsoever, although such uninterrupted measurements may be included in the term "continuous." For example, the continuous measurements may be digital measurements in some embodiments, in which case such measurements are not literally uninterrupted but may instead be sampled at a rate provided by the instrumentation or software controlling the instrumentation. In other embodiments, the continuous measurements may be analog but may occur at defined intervals or at some defined or maximum rate.

In step 104, first and second fluid pressure values are obtained at the first and second stations, respectively. The first and second fluid pressure values may be measured by a measuring device in the tool, may be obtained from prior well logs, or may be obtained in other ways.

In step 106, at least one gravity value is obtained based on the first and second stations. For example, step 106 may involve calculating an average acceleration due to gravity for a vertical depth between the first and second stations. Alternatively, the gravity value may be calculated based on gravity measurements made at the first and second stations by the tool, may be obtained from prior well logs, or may be obtained in other ways.

In step 108, a vertical distance Δz may be calculated based on the fluid density values, the first and second pressure values, and the gravity value as illustrated in Equation 3. It is understood that the steps 102, 104, and 106 need not occur in the particular order shown as long as the information needed for the calculation of Δz is obtained prior to step 108.

Figure 1B:
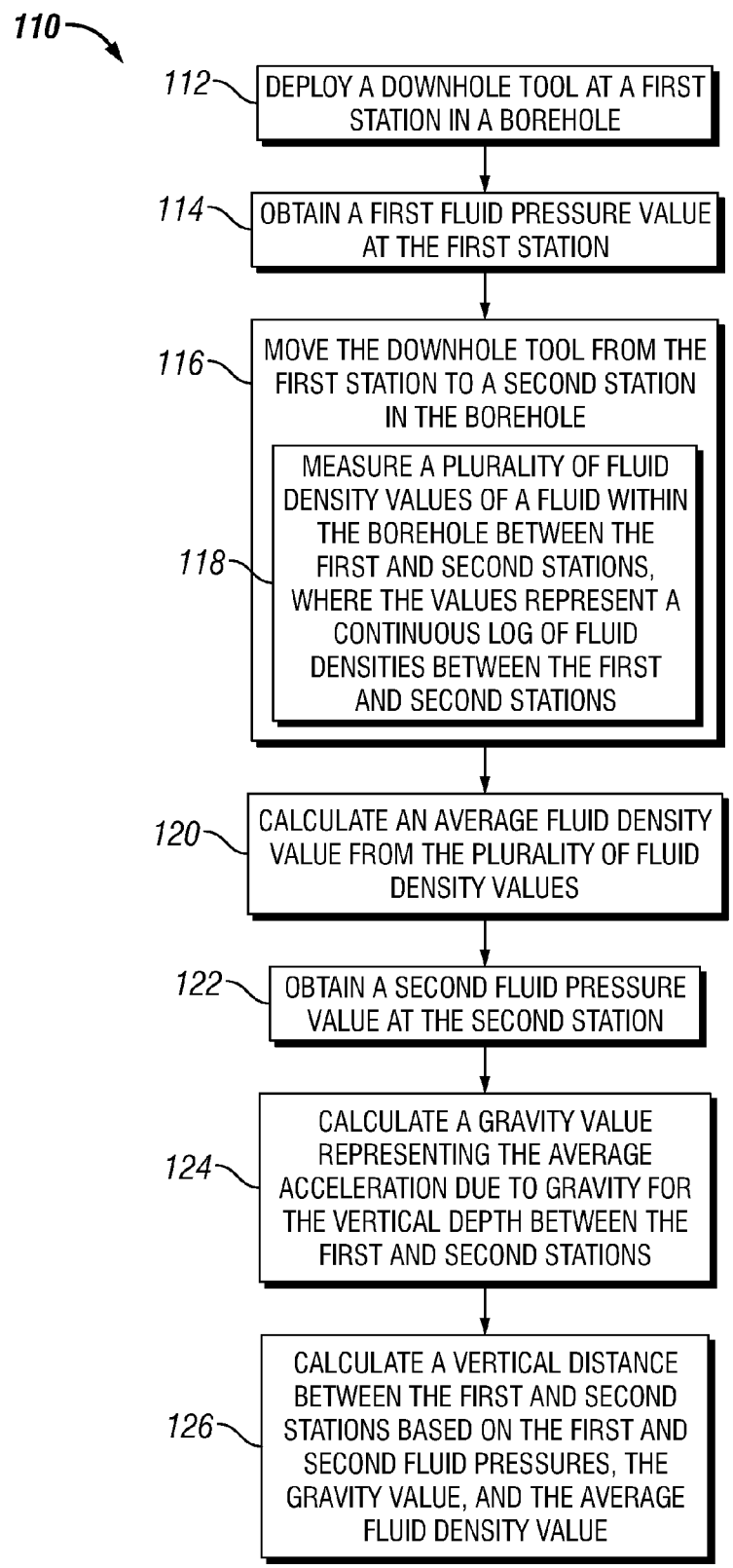
FIG. 1B is a flow chart diagram of at least a portion of a method according to one or more aspects of the present disclosure.

FIG. 1B is a flow-chart diagram of at least a portion of a method 110 according to one or more aspects of the present disclosure. The method 110 may be or comprise a process for measuring fluid density in a borehole. These fluid density measurements may then be used to obtain an accurate vertical distance from a differential pressure measurement in the presence of varying fluid density.

In step 112, a downhole tool is deployed to a first station within the borehole. As will be described later in greater detail, the downhole tool may be conveyed by wireline, slick line, drill-pipe, tubing, and/or any other means (not shown) used in the industry. The tool may include various types of measurement instruments for measuring the fluid density of a fluid within the borehole, such as a gradio-manometer, a density-viscosity vibrating rod, a Helmholtz acoustic resonator, acoustic sources and detectors, and/or radiation sources and detectors.

In step 114, a first fluid pressure value is obtained for the first station. The fluid pressure value may be measured by a measuring device in the tool, may be obtained from prior well logs, or may be obtained in other ways.

In step 116, the tool is moved from the first station to a second station. One of the two stations may be at or near the surface in some embodiments. During this time, as illustrated in step 118, the measurement instrument(s) within the tool are used to measure a plurality of fluid density values of the fluid within the borehole. The measurements may be made while the tool is moving and/or when the tool is stopped. The values may represent a continuous log of fluid densities between the first and second stations.

In step 120, an average fluid density value may be calculated based on the plurality of fluid density values obtained in step 118. This step may be based on Equation 5 as described above or may use another method for calculating the average fluid density. Although not shown in the present embodiment, some embodiments may include a determination step prior to step 120. In such a determination step, a determination may be made as to whether the average fluid density value should be calculated. This determination may be based on, for example, whether the fluid in the borehole is inhomogeneous or whether a distance between the two stations exceeds a certain threshold. For example, relatively large distances between the two stations may increase the likelihood that the fluid is inhomogeneous and so may trigger the averaging of step 120. If the determination step determines that averaging is not needed, the method 110 may skip step 120 and from step 118 go directly to step 122.

In step 122, a second fluid pressure value is obtained for the second station.

In step 124, a gravity value may be calculated. In the present example, the calculated gravity value is the average acceleration due to gravity for the vertical depth between the first and second stations.

In step 126, the vertical distance Δz may be calculated based on the pressure values, the gravity value, and the average fluid density value. For example, the vertical distance Δz may be calculated as illustrated in Equation 3.

In later steps (not shown), Δz may be used to calculate formation bulk density as illustrated in Equation 1 or may be used for any other desired purpose. For example, the calculated vertical distance may be applied to a seismic map for precise time-to-depth correlation.

The fluid density may also be used for purposes other than the calculation of Δz. For example, the fluid density may be used to determine water salinity and the water salinity determination may be used for such purposes as the correction of resistivity, neutron sigma, neutron porosity, and gamma-gamma density logs. The fluid density may also be used to determine the location of gas influx and water influx, to determine the quality of drilling fluid, to determine an oil type, and/or to detect the presence of substances such as sand, gas bubbles, and hydrogen sulfide.

Figure 2A:
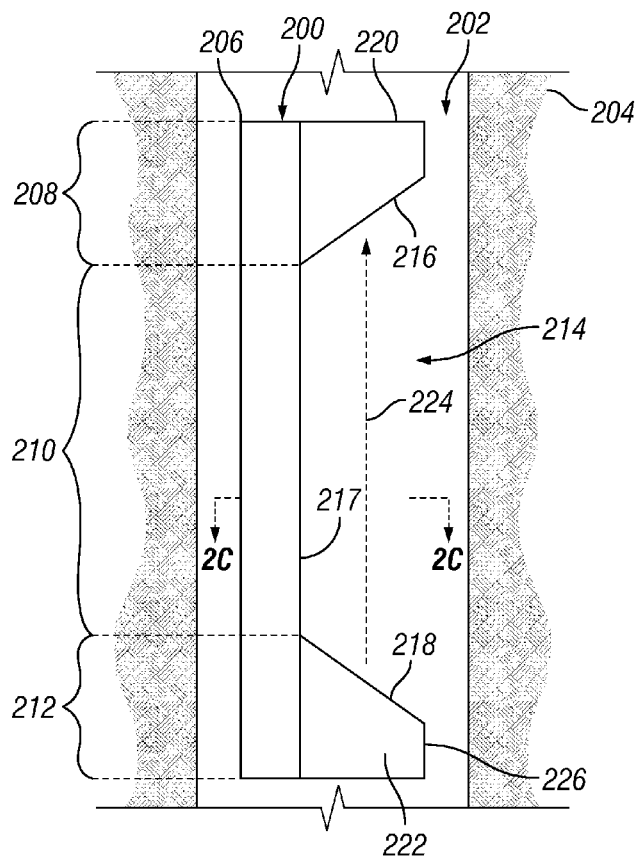
FIG. 2A is a schematic view of an apparatus according to one or more aspects of the present disclosure.

FIG. 2A is a schematic of one embodiment of a downhole tool 200 according to one or more aspects of the present disclosure. The tool 200 may be used in a borehole 202 formed in a geological formation 204, and may be conveyed by wireline, drill-pipe, tubing, and/or any other means (not shown) used in the industry. The tool 200 comprises a housing 206 that contains multiple components configured to measure fluid density in the borehole 202 as described, for example, with respect to the method 100 of FIG. 1A.

As illustrated in FIG. 2A, the tool 200 includes a detection section 208, an intermediate section 210, and a source section 212. In the present example, the detection section 208 and the source section 212 both have a substantially cylindrical cross-section. The intermediate section 210, which couples the detection section 208 and the source section 212, has a non-cylindrical cross-section. For example, the intermediate section 210 may have a "D-shaped" cross-section with the curve of the "D" corresponding to a curve of an outer surface of the detection section 208 and source section 212.

This D shape provides a fluid sample area 214 in the otherwise cylindrical shape of the tool 200. The fluid sample area 214 provides access for components within the detection section 208 and the source section 212 to any fluids that may be in the borehole 202, while maintaining the pressure integrity of the pressure housing 206. More specifically, the D-shaped constriction in the housing 206 may provide a good sampling of the borehole fluid as the tool 200 is pulled up in the borehole 202. The movement of the tool 200 in the borehole 202 may ensure that fluid sampled in a lower portion of the borehole 202 is quickly and efficiently replaced by fluid from the present depth of the tool 200 in the borehole 202. In this embodiment, no mechanical systems, such as pumps, are needed for sampling the fluid.

It is understood that the intermediate section 210 may be configured with many different cross-sections and may provide different embodiments of the fluid sample area 214. For example, in some embodiments, the intermediate section 210 may have a substantially cylindrical cross-section with one or more slots, gaps, or other openings to allow fluid from the borehole 202 to enter and exit a chamber that forms the fluid sample area 214 within the intermediate section 210. Accordingly, the present disclosure is not limited to the intermediate section 210 having a D-shaped cross-section as described herein.

The fluid sample area 214 is adjacent to a surface 216 of the detection section 208, a surface 217 (i.e., the straight portion of the "D") of the intermediate section 210, and a surface 218 of the source section 212. The two surfaces 216 and 218 face one another across the fluid sample area 214. In the present example, the two surfaces 216 and 218 are illustrated as being sloped, but it is understood that this slope may be absent in some embodiments. It is also understood that the divisions between the detection section 208, the intermediate section 210, and the source section 212 are shown for purposes of example, but may be located elsewhere or may be absent. For example, the sloped surfaces 216 and 218 may be viewed as surfaces of the intermediate section 210 in some embodiments. Accordingly, the locations and delineation of the detection section 208, the intermediate section 210, and the source section 212 relative to the tool 200 and to one another are not intended to be limiting.

The detection section 208 includes detection components 220 and the source section 212 contains source components 222. It is understood that these two sections 208 and 212 may be reversed in some embodiments. The source components 222 may be configured to produce acoustic, ionizing radiation, and/or other types of emissions that exit the source section 222 via the surface 218 and travel across the fluid sample area 214 to the surface 216 as illustrated by arrow 224. The detection components 220, which may correspond in type to the source components 222, detect the emissions. As the fluid sample area 214 is open to fluid in the borehole 202, the emissions from the source components 222 will pass through the fluid before reaching the detection components 220. Accordingly, the detected emissions may be used to measure fluid density of the borehole fluid as described with respect to the method 100 of FIG. 1A.

Figure 2C:
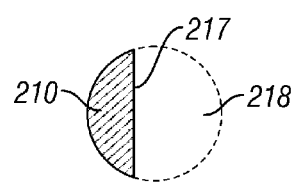
FIG. 2C is a cross-sectional view of one embodiment of the apparatus of FIG. 2A as taken along line A-A of FIG. 2A according to one or more aspects of the present disclosure.
Figure 2B:
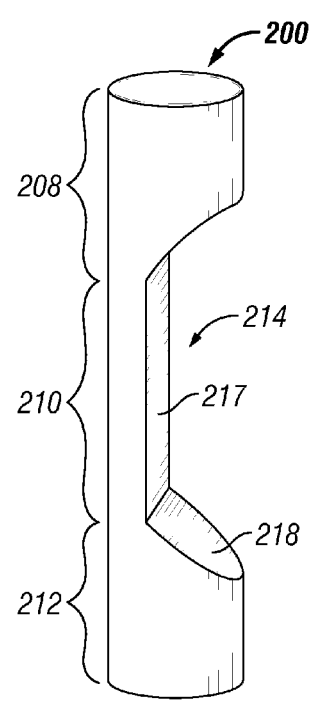
FIG. 2B is a perspective view of one embodiment of the apparatus of FIG. 2A according to one or more aspects of the present disclosure.

FIG. 2B is a perspective view of one embodiment of the downhole tool 200 of FIG. 2A according to one or more aspects of the present disclosure. As illustrated in FIG. 2B, the D-shaped cross-section of the intermediate section 210 provides the fluid sample area 214 that exposes surfaces of the detection section 208 and the source section 212 to fluid in the borehole 202.

FIG. 2C is a schematic of one embodiment of the downhole tool 200 of FIG. 2A taken along lines A-A of FIG. 2A according to one or more aspects of the present disclosure. As illustrated in FIG. 2C, the D-shaped cross-section of the intermediate section 210 may provide a hollow column through which wires (not shown) may be run or within which other components (not shown) may be placed.

Figure 3:
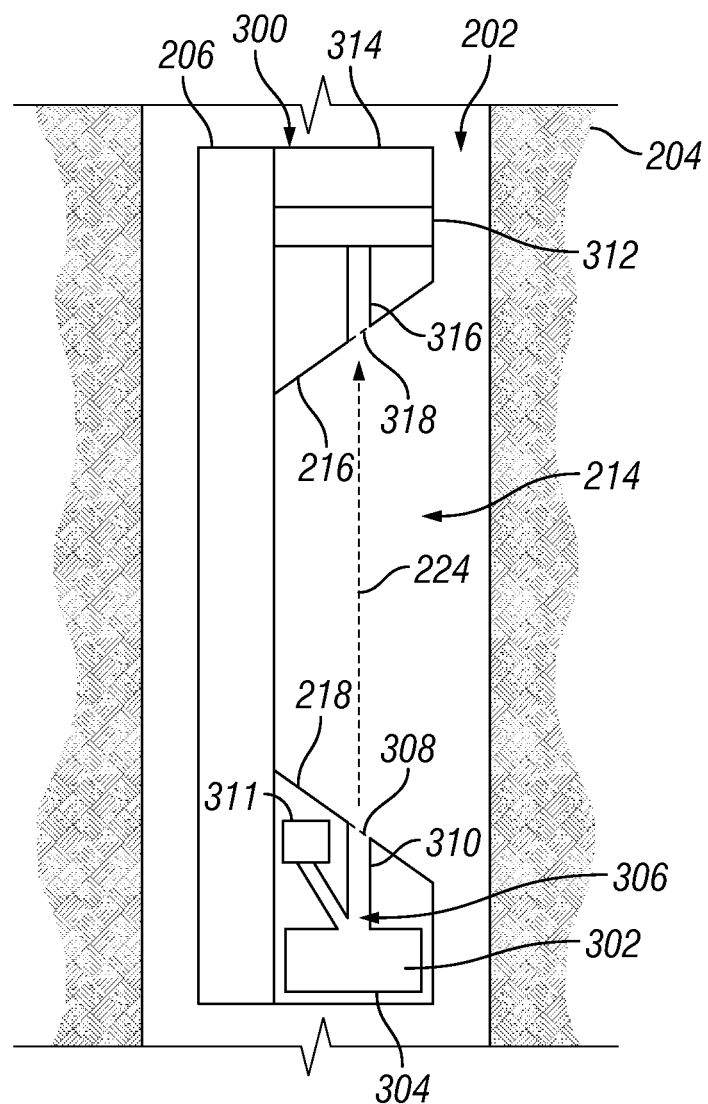
FIG. 3 is a schematic view of an apparatus according to one or more aspects of the present disclosure.

FIG. 3 is a schematic of one embodiment of a downhole tool 300 according to one or more aspects of the present disclosure. In the present example, the tool 300 may be similar to the tool 200 of FIG. 2A and similar parts will not be discussed in detail in the following description.

The source components 222 in the tool 300 include a radiation source 302. The radiation source 302 may be an electronically driven radiation source (e.g., x-rays or gamma-rays), a chemical radiation source (e.g., $^{137}$Cs, $^{133}$Ba and $^{153}$Gd), and/or any other radiation source that may be configured for use in the tool 300. For purposes of example, the radiation source 302 is an x-ray generator.

The radiation source 302 may be surrounded by shielding 304. The shielding 304 may, for example, provide safety for personnel from radiation when operating at the surface and may aid in preventing the scattering of photons into the detection components 220 via paths that are not through the fluid. The shielding 304 may include an opening 306 facing the surface 218 and this opening may provide collimation of the photon beam, which may aid in preventing scattered photons from reaching the detection components 220.

A window 308 may be located in the surface 218 to facilitate the emission of the x-rays through the housing 206. For example, the housing 206 may be constructed of relatively thick steel to withstand high pressures in the borehole 202 and the steel may attenuate the x-rays. Accordingly, the presence of the window 308 may aid in maintaining an adequate count rate in the detection components 220. The window 308 may be provided by a thinned section of steel, a light metal insert such as titanium, beryllium, silicon, or aluminum, a ceramic insert such as boron carbide or aluminum oxide, and/or any other suitable material and/or construction method that minimizes attenuation of the x-rays without comprising the pressure integrity of the housing 206.

In some embodiments, a collimator 310 may be positioned between the radiation source 302 (e.g., the x-ray generator) and the window 308. The collimator 310 may define an approximately parallel beam of emitted photons and may aid in minimizing or eliminating scattered photons from reaching the detection components 220.

The source components 222 may further comprise a flux monitor 311, which intercepts a portion of the radiation emitted from the source. The flux monitor 311 indicates the emission rate of the radiation source 302 which is the denominator in the calculation of the attenuation ratio.

The detection components 220 may include various types of detectors, such as scintillation, photodiode, and/or semiconductor detectors. Examples of suitable scintillators include sodium iodide, gadolinium ortho-silicate, lutetium aluminate perovskite, and cesium iodide. An example of a semiconductor x-ray detector is cadmium zinc telluride. It is understood that many types of detectors may be used as long as they are capable of detecting emissions from the corresponding source components 222. In the present example, the detector is a scintillator 312.

The scintillator 312 may be optically coupled to a photo-detector 314, which may be a photo-diode, a photomultiplier tube, a micro-channel plate detector, or another type of photo-detector. Because the borehole 202 may be relatively hot, the choice of detector may be limited by the operating temperature. A collimator 316 and a window 318 may be provided for the detection components 220 as described with respect to the source components 222.

In operation, the scintillator 312 is excited by incoming x-rays from the x-ray generator that forms the radiation source 302 in the present example. The excitation produces luminescence that is detected by the photo-detector 314.

The detected luminescences may be counted to determine a detection rate. This detection rate along with the source emission rate obtained with the flux monitor 311 are used to determine an attenuation ratio which is in turn used in identifying the fluid density of the fluid in the borehole 202 through which the x-rays passed.

In the present example, factors in determining the accuracy and precision of the measurements provided by the tool 300 include source strength, source energy, distance from source to detector and detector solid angle. It may be desirable to optimize one or more of these factors to ensure an accurate measurement in a reasonable amount of time and to ensure good sensitivity to changes in fluid density. For example, in the current embodiment, the x-ray generator that forms the radiation source 302 may have an energy of eighty-five keV and a dual energy measurement created using a barium filter may be used to correct for the photo-electric absorption of chlorine. Boron carbide windows 308 and 318 may be used, and the spacing from the radiation source 302 to the scintillator 312 may be approximately ten centimeters.

Figure 4A:
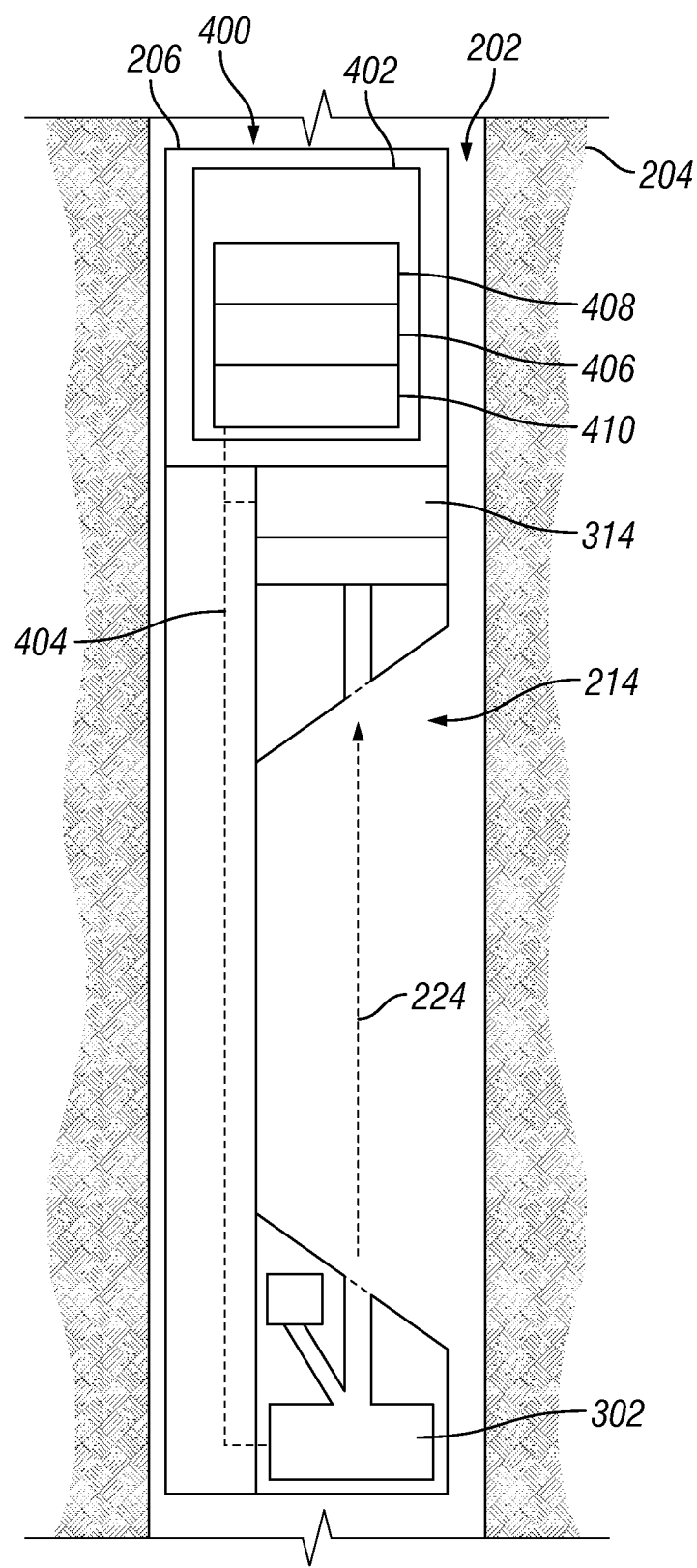
FIG. 4A is a schematic view of an apparatus according to one or more aspects of the present disclosure.

FIG. 4A is a schematic of one embodiment of a downhole tool 400 according to one or more aspects of the present disclosure. In the present example, the tool 400 may be similar to the tool 300 of FIG. 3 and similar parts will not be discussed in detail in the following description.

In the present example, the tool 400 includes a control module 402 that may be in wireless and/or wired communication via communication path(s) 404 with one or both of the detection components 220 and the source components 222. It is understood that the communication path 404 may be coupled to the radiation source 404 in embodiments having an electronic radiation source, but may not be coupled to the radiation source in embodiments having a chemical radiation source. The control module 402 may also be in signal communication with one or more components (not shown) positioned outside of the tool 400 in the borehole 202 and/or outside of the borehole 202 on the surface.

The control module 402 may include a central processing unit (CPU) and/or other processor 406 coupled to a memory 408 in which are stored instructions for the acquisition and/or storage of the measurements, as well as instructions for other functions of the tool 400. Instructions for performing calculations based on the measurements may also be stored in the memory 408 for execution by the CPU 406. The CPU 406 may also be coupled to a communications interface 410 for the wired and/or wireless communications via the communication path(s) 404. It is understood that the CPU 406, memory 408, and communications interface 410 may be combined into a single device or may be distributed in many different ways. For example, the CPU 406, memory 408, and communications interface 410 may be separate components placed in a housing forming the control module 402, may be separate components that are distributed throughout the tool 400 and/or on the surface, or may be contained in an integrated package such as an application specific integrated circuit (ASIC). Means for powering the tool 400, receiving information from the surface and transferring information to the surface, and/or performing other functions unrelated to the fluid density measurements of the present disclosure may also be incorporated in the control module 402.

It is understood that measurements made by the tool 400 may be automated with the aid of the control module 402 and/or a controller located on the surface and connected to the tool 400 via some telemetry means. In other embodiments, the measurements may also be aided or accomplished with human interpretation of the data and judgment and with the aid of a telemetry means establishing communication of data and instructions between the tool 400 and the interpreter.

Figure 4B:
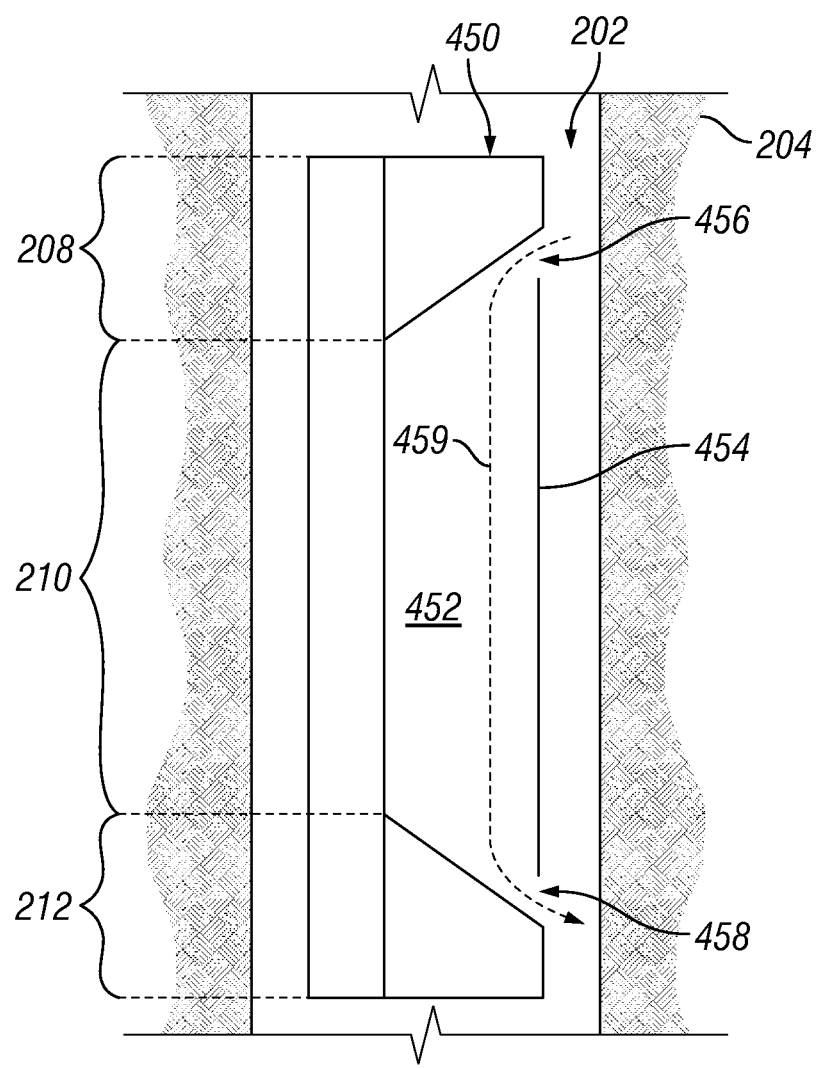
FIG. 4B is a schematic view of an apparatus according to one or more aspects of the present disclosure.

FIG. 4B is a schematic of another embodiment of a downhole tool 450 according to one or more aspects of the present disclosure. In the present embodiment, the tool 450 is similar to the tool 200 of FIG. 2A, but the tool 450 has a substantially cylindrical cross-section and the fluid sample area 214 of the tool 450 is not fully open to the borehole 202. More specifically, in the present embodiment, the tool 450 includes a chamber 452 in the D-shaped area that is formed by a sidewall 454. Openings 456 and 458 in the sidewall 454 provide a fluid flow path 459 for borehole fluid.

Figure 4C:
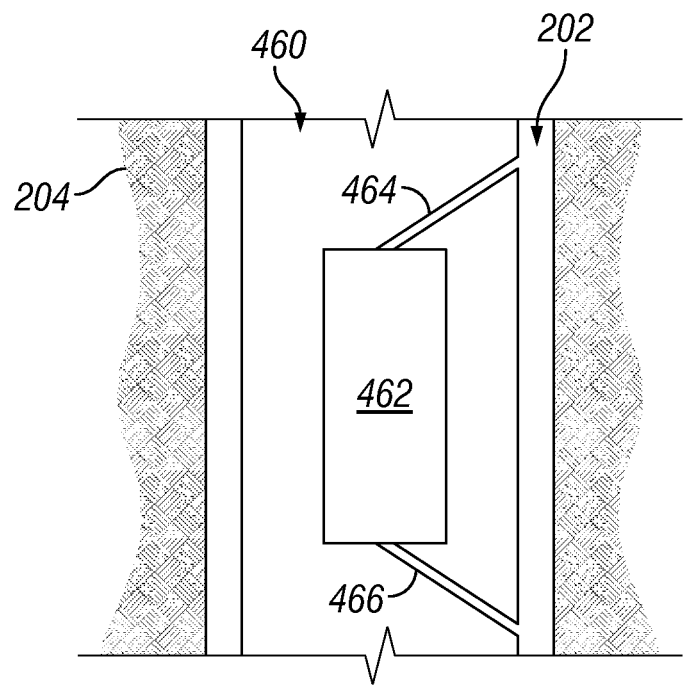
FIG. 4C is a schematic view of an apparatus according to one or more aspects of the present disclosure.

FIG. 4C is a schematic of another embodiment of a downhole tool 460 according to one or more aspects of the present disclosure. In the present embodiment, the tool 460 does not have detection components 220 and source components 222 as described with respect to FIG. 2A. Instead, the tool 460 may have a substantially cylindrical cross-section having a densitometer 462 positioned therein. The densitometer 462 is coupled to an inflow line 464 and an outflow line 466. The inflow line 464 may be used to provide borehole fluid from the borehole 202 to the densitometer 462. The outflow line 466 may be used to remove fluid from the densitometer 462. It is understood that the inflow line 464 and outflow line 466 may not be directly coupled to the exterior of the tool 460 as shown in FIG. 4C, but may be coupled to other flow lines (not shown) within the tool. Furthermore, the angles of the inflow and outflow lines 464 and 466 may be altered from those illustrated. In some embodiments, pumps or other fluid movement mechanisms (not shown) may be used to move borehole fluid to the densitometer 462.

Figure 4D:
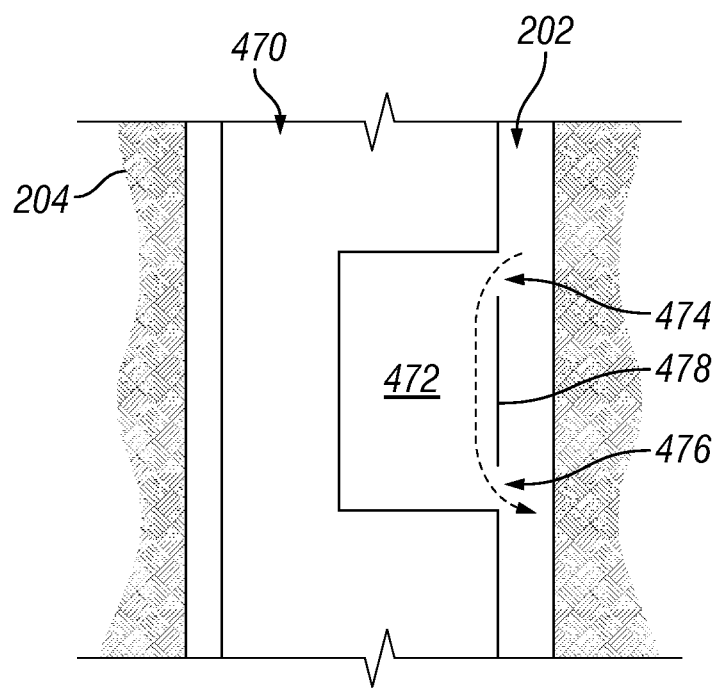
FIG. 4D is a schematic view of an apparatus according to one or more aspects of the present disclosure.

FIG. 4D is a schematic of another embodiment of a downhole tool 470 according to one or more aspects of the present disclosure. In the present embodiment, the tool 470 does not have detection components 220 and source components 222 as described with respect to FIG. 2A. Instead, the tool 470 may have a substantially cylindrical cross-section having a densitometer 472 positioned therein. The densitometer 472 may be positioned so as to receive borehole fluid from the borehole 202 via an opening 474. The borehole fluid enters the densitometer 472 via the opening 474 and exits via another opening 476, thereby creating a fluid flow path 478.

It is understood that many different modifications may be made to the downhole tools 200 of FIG. 2A, 450 of FIG. 4B, 460 of FIG. 4C, and 470 of FIG. 4D. Modifications may also be made to the detection components 220 and source components 222, to the densitometers 462 and 472 of FIGS. 4C and 4D, and to other embodiments described herein. For example, the source components 222 and detection components 220 may include acoustic sources and detectors, radiation sources and detectors, and/or any other suitable means for obtaining fluid density measurements. The densitometers 462 and 472 may comprise a gradio-manometer, a density-viscosity vibrating rod or a Helmholtz acoustic resonator. Furthermore, it is understood that some source/detector selections may involve changes to the physical configuration of the tool 200. For example, a Helmholtz acoustic resonator, for which density is calculated from acoustic impedance and resonant acoustic frequency, may be configured as a closed cylinder with ports at the top and bottom for the ingress/egress of borehole fluid. Other embodiments may include a cylindrical resonator with one or more slits down the side to aid in the exchange of borehole fluid. These and other configurations may also be used for the radiation components and/or acoustic components.

Still other embodiments may provide the detection components 220 and the source components 222 arranged around or on opposing sides of a longitudinal axis of the tool 200, rather than vertically as illustrated in FIG. 2A. In such embodiments, fluid may pass between the detection components 220 and the source components 222 as previously described. Other embodiments may use one or more pumps or other fluid control means to control the flow of fluid from the borehole 202. Accordingly, many different configurations are possible.

Furthermore, the tool 200 may be deployed and operated in combination with other tools to form a tool string in the case of wireline, coiled tubing, or tractor conveyance and a bottom-hole assembly in the case of Logging While Drilling. For example, the tool 200 or components of the tool 200 may be combined with one or more of a borehole gravity measurement tool, a borehole seismic measurement tool, a borehole, surface-to-borehole or cross-well electro-magnetic measurement tool, and a formation pressure measurement tool, for the purpose of obtaining a suite of deep reading measurements as described in U.S. Patent Application Publication No. 2009/0164187, which is hereby incorporated by reference in its entirety. Combinations of tools may be constructed on the basis of a common need to take measurements only while the tool string is stationary (so-called station measurements), on the basis of a common need for precision position indexing, on the basis of a common purpose for the set of measurements (such as for reservoir model construction), on the basis of comparing measurements with redundancy such as gravity-derived density and gamma-gamma density, on the basis of scheduling of borehole access, combinations of the aforementioned bases or any other basis determined by a user of the tool 200.

Figure 5A:
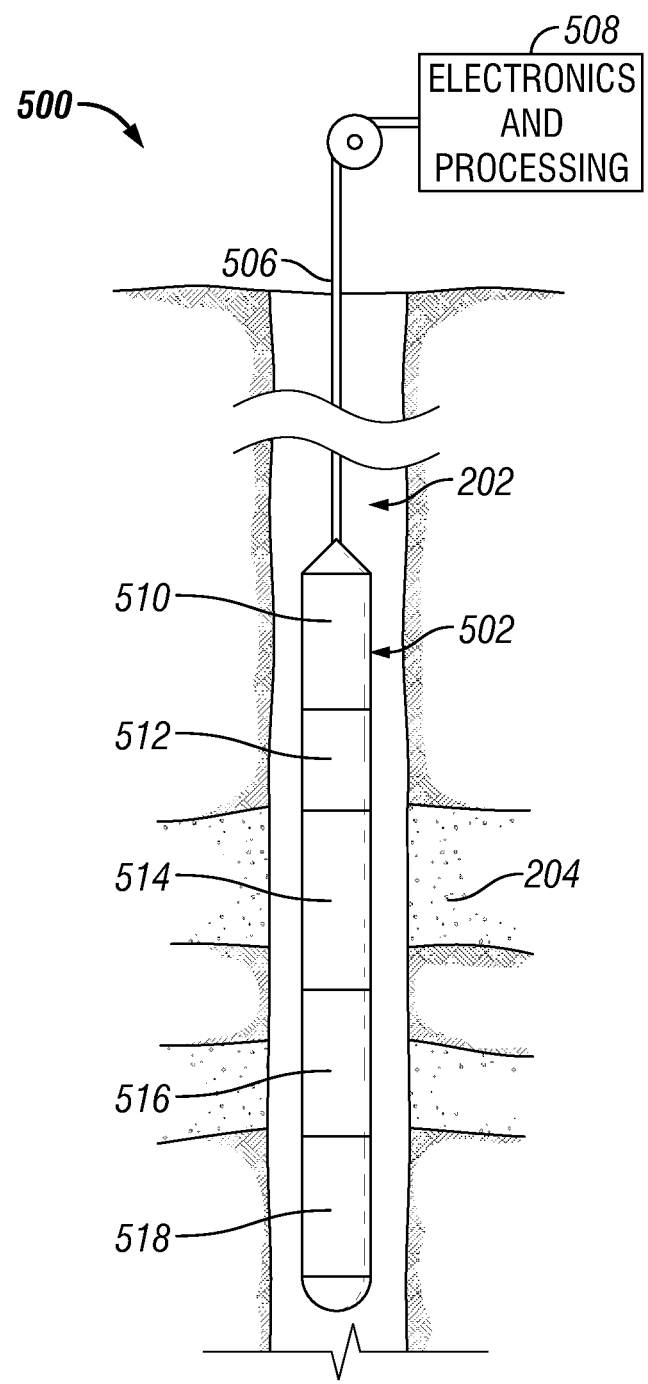
FIG. 5A is a schematic view of an apparatus according to one or more aspects of the present disclosure.

FIG. 5A is a schematic view of apparatus according to one or more aspects of the present disclosure, including one embodiment of an environment 500 with a wireline tool 502 in which aspects of the present disclosure may be implemented. The wireline tool 502 may be similar or identical to the downhole tool 200 of FIG. 2A. The wireline tool 502 is suspended in a borehole 202 from the lower end of a cable 506 that is spooled on a winch (not shown) at the Earth's surface. At the surface, the cable 506 is communicatively coupled to an electronics and processing system 508. The wireline tool 502 includes an elongated body 510. Additional modules 512, 514, 516 and 518 (e.g., components described above with respect to FIG. 2A) may also be included in the tool 502. In the illustrated example, the electronics and processing system 508 and/or a downhole control system (e.g., the control module 402 of FIG. 4A) may be configured to control various components of the tool 502.

Figure 5B:
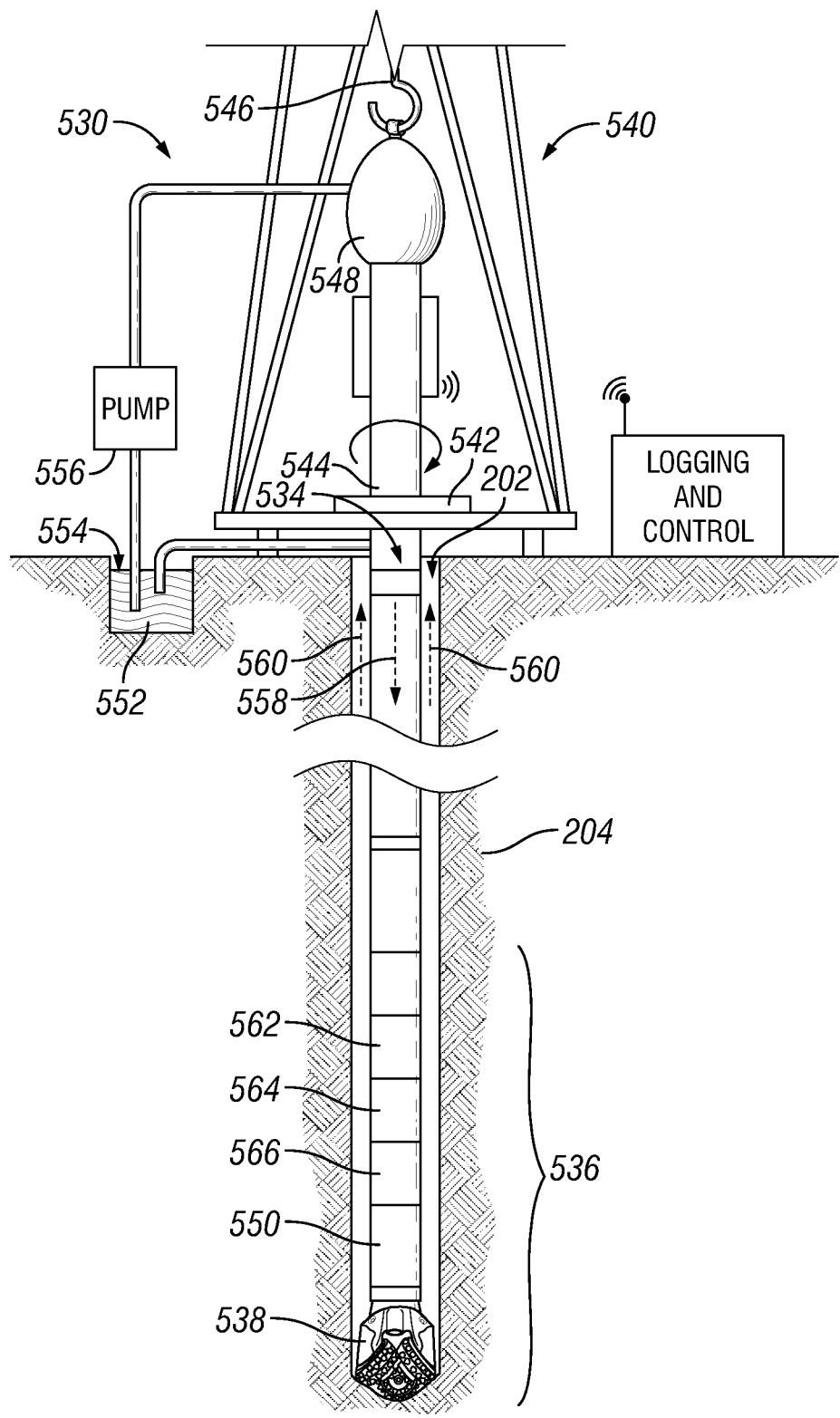
FIG. 5B is a schematic view of an apparatus according to one or more aspects of the present disclosure.

FIG. 5B is a schematic view of apparatus according to one or more aspects of the present disclosure, including one embodiment of a wellsite system environment 530 in which aspects of the present disclosure may be implemented. The wellsite can be onshore or offshore. A borehole 202 is formed in subsurface formations (e.g., the formation 204 of FIG. 2A) by rotary drilling and/or directional drilling.

A drill string 534 is suspended within the borehole 202 and has a bottom hole assembly 536 that includes a drill bit 538 at its lower end. The surface system includes platform and derrick assembly 540 positioned over the borehole 202, the assembly 540 including a rotary table 542, kelly 544, hook 546 and rotary swivel 548. The drill string 534 is rotated by the rotary table 542, energized by means not shown, which engages the kelly 544 at the upper end of the drill string. The drill string 534 is suspended from the hook 546, attached to a traveling block (not shown), through the kelly 544 and the rotary swivel 548, which permits rotation of the drill string relative to the hook. As is well known, a top drive system could alternatively be used.

The surface system further includes drilling fluid or mud 552 stored in a pit 554 formed at the well site. A pump 556 delivers the drilling fluid 552 to the interior of the drill string 534 via a port in the swivel 548, causing the drilling fluid to flow downwardly through the drill string 534 as indicated by the directional arrow 558. The drilling fluid 552 exits the drill string 534 via ports in the drill bit 538, and then circulates upwardly through the annulus region between the outside of the drill string and the wall of the borehole 202, as indicated by the directional arrows 560. In this well known manner, the drilling fluid 552 lubricates the drill bit 538 and carries formation cuttings up to the surface as it is returned to the pit 554 for recirculation.

The bottom hole assembly 536 may include a logging-while-drilling (LWD) module 562, a measuring-while-drilling (MWD) module 564, a roto-steerable system and motor 550, and drill bit 538. The LWD module 562 may be housed in a special type of drill collar, as is known in the art, and can contain one or more known types of logging tools. It is also understood that more than one LWD and/or MWD module can be employed, e.g., as represented by LWD tool suite 566. (References, throughout, to a module at the position of 562 can alternatively mean a module at the position of 566 as well.) The LWD module 562 (which may be similar or identical to the tool 200 shown in FIG. 2A or may contain components of the tool 200) may include capabilities for measuring, processing, and storing information, as well as for communicating with the surface equipment. In the present embodiment, the LWD module 562 includes measurement devices, such as the fluid density measurement components described with respect to FIG. 2A.

The MWD module 564 may also be housed in a special type of drill collar, as is known in the art, and can contain one or more devices for measuring characteristics of the drill string 534 and drill bit 538. The MWD module 564 further includes an apparatus (not shown) for generating electrical power to the downhole system. This may typically include a mud turbine generator powered by the flow of the drilling fluid, it being understood that other power and/or battery systems may be employed. The MWD module 564 may include one or more of the following types of measuring devices: a weight-on-bit measuring device, a torque measuring device, a vibration measuring device, a shock measuring device, a stick/slip measuring device, a direction measuring device, and an inclination measuring device.

In view of all of the above and the figures, it should be readily apparent to those skilled in the art that the present disclosure introduces a method for obtaining fluid density values for a fluid between first and second stations in a borehole comprising: deploying a downhole tool at the first station; moving the downhole tool from the first station to the second station; and measuring a plurality of fluid density values of the fluid within the borehole between the first and second stations using a fluid density measurement device in the downhole tool, wherein the plurality of fluid density values represent a continuous log of fluid densities between the first and second stations. The method may further comprise obtaining first and second fluid pressure values of the first and second stations, respectively; calculating a gravity value based on a depth of the first and second stations; and calculating a vertical distance between the first and second stations based on the first and second fluid pressure values, the calculated gravity value, and the plurality of fluid density values. The method may further comprise calculating an average fluid density for the fluid between the first and second stations using the plurality of fluid density values, wherein the average fluid density is used when calculating the vertical distance. The average fluid density may be calculated only if the fluid is non-homogeneous. Calculating the gravity value based on the depth of the first and second stations may include calculating an average acceleration due to gravity based on a vertical depth between the first and second stations. The plurality of fluid density measurements may be obtained while the downhole tool is moving within the borehole between the first and second stations. The fluid density measurement device may comprise a radiation source and a radiation detector, and obtaining the plurality of fluid density measurements may include detecting radiation that is emitted by the radiation source through the fluid and received by the radiation detector. The radiation source may be one of an x-ray source and a gamma-ray source. The fluid density measurement device may comprise an acoustic source and an acoustic detector, and obtaining the plurality of fluid density measurements may include detecting an acoustic signal that is emitted by the acoustic source through the fluid and received by the acoustic detector. The fluid density measurement device may comprise an acoustic resonator, and obtaining the plurality of fluid density measurements may be based on an acoustic impedance and a resonant acoustic frequency of the acoustic resonator.

The present disclosure also introduces a downhole tool for use in a borehole comprising: a housing; a radiation source disposed within a first section of the housing, wherein the radiation source is configured to emit radiation in a radiation path out of the first section and towards a second section of the housing; a radiation detector disposed within the second section of the housing, wherein the radiation detector is configured to detect radiation emitted by the radiation source; and an intermediate section of the housing coupling the first and second sections, wherein a fluid sample area of the intermediate section is open to fluid within the borehole and positioned between the radiation source and the radiation detector so as to include the radiation path, and wherein the fluid sample area is configured to allow the fluid to freely pass through the radiation path between the radiation source and the radiation detector as the downhole tool is moved within the borehole. The first and second sections of the housing may have a substantially circular cross-section, and the intermediate section may have a substantially "D-shaped" cross-section with a curved portion of the D-shape corresponding to a curve of the circular cross-sections of the first and second sections. A transition between the substantially circular cross-section of each of the first and second sections and the substantially "D" shaped cross-section of the intermediate section may be angled. At least one of the first and second sections may further include a collimator. The radiation detector may comprise a scintillator positioned to receive radiation via the radiation path and a photodetector coupled to the scintillator. At least one of the first and second sections may include a window in the housing proximate to the radiation source and radiation detector, respectively. The radiation source may be an x-ray source and the radiation detector may be an x-ray detector.

The present disclosure also introduces a downhole tool for use in a borehole comprising: a housing; a densitometer disposed within the housing so as to have access to fluid from the borehole; a processor disposed within the housing and coupled to the densitometer; and a memory coupled to the processor and configured to store a plurality of instructions for execution by the processor, the instructions comprising instructions for using the densitometer to measure a plurality of fluid density values of the fluid within the borehole between first and second stations, wherein the plurality of fluid density values represent a continuous log of fluid densities between the first and second stations. The densitometer may be selected from the group consisting of an acoustic densitometer, a gradio-manometer, and a density-viscosity rod. The acoustic densitometer may comprise an acoustic source disposed within a first section of the housing, wherein the acoustic source is configured to emit an acoustic signal in a path out of the first section and towards a second section of the housing; and an acoustic detector disposed within the second section of the housing, wherein the acoustic detector is configured to detect the acoustic signal emitted by the acoustic source. The downhole tool may further comprise an intermediate section of the housing coupling the first and second sections, wherein a fluid sample area of the intermediate section is open to fluid from the borehole, and wherein the fluid sample area is positioned within the intermediate section to allow the fluid to pass through the acoustic signal between the acoustic source and the acoustic detector. The downhole tool may be configured for conveyance in a wellbore via at least one of a wireline and a drill pipe.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

What is claimed is:

1. A method for obtaining fluid density values for a fluid between first and second stations in a borehole comprising:
  deploying a downhole tool at the first station;
  moving the downhole tool from the first station to the second station;
  measuring a plurality of fluid density values of the fluid within the borehole between the first and second stations using a fluid density measurement device in the downhole tool, wherein the plurality of fluid density values represent a continuous log of fluid densities between the first and second stations;
  obtaining first and second fluid pressure values of the first and second stations, respectively;
  calculating a gravity value based on a depth of the first and second stations;
  calculating a vertical distance between the first and second stations based on the first and second fluid pressure values, the calculated gravity value, and the plurality of fluid density values; and
  calculating an average fluid density for the fluid between the first and second stations using the plurality of fluid density values, if the vertical distance between the first and second stations indicates that the fluid is non-homogenous.

2. The method of claim 1 wherein the average fluid density is calculated only if the fluid is non-homogeneous.

3. The method of claim 1 wherein calculating the gravity value based on the depth of the first and second stations includes calculating an average acceleration due to gravity based on a vertical depth between the first and second stations.

4. The method of claim 1 wherein the plurality of fluid density measurements are obtained while the downhole tool is moving within the borehole between the first and second stations.

5. The method of claim 1 wherein the fluid density measurement device comprises a radiation source and a radiation detector, and wherein obtaining the plurality of fluid density measurements includes detecting radiation that is emitted by the radiation source through the fluid and received by the radiation detector.

6. The method of claim 5 wherein the radiation source is one of an x-ray source and a gamma-ray source.

7. The method of claim 1 wherein the fluid density measurement device comprises an acoustic source and an acoustic detector, and wherein obtaining the plurality of fluid density measurements includes detecting an acoustic signal that is emitted by the acoustic source through the fluid and received by the acoustic detector.

8. The method of claim 1 wherein the fluid density measurement device comprises an acoustic resonator, and wherein obtaining the plurality of fluid density measurements is based on an acoustic impedance and a resonant acoustic frequency of the acoustic resonator.

9. A downhole tool for use in a borehole comprising:
 a housing;
 a densitometer disposed within the housing so as to have access to fluid from the borehole;
 a processor disposed within the housing and coupled to the densitometer; and
 a memory coupled to the processor and configured to store a plurality of instructions for execution by the processor, the instructions comprising instructions for
  using the densitometer to measure a plurality of fluid density values of the fluid within the borehole between first and second stations, wherein the plurality of fluid density values represent a continuous log of fluid densities between the first and second stations,
  obtaining first and second fluid pressure values of the first and second stations, respectively,
  calculating a gravity value based on a depth of the first and second stations;
  calculating a vertical distance between the first and second stations based on the first and second fluid pressure values, the calculated gravity value, and the plurality of fluid density values, and
  calculating an average fluid density for the fluid between the first and second stations using the plurality of fluid density values, if the vertical distance between the first and second stations indicates that the fluid is non-homogenous.

10. The downhole tool of claim 9 wherein the densitometer is selected from the group consisting of an acoustic densitometer, a gradio-manometer, and a density-viscosity rod.

11. The downhole tool of claim 10 wherein the acoustic densitometer comprises:
 an acoustic source disposed within a first section of the housing, wherein the acoustic source is configured to emit an acoustic signal in a path out of the first section and towards a second section of the housing; and
 an acoustic detector disposed within the second section of the housing, wherein the acoustic detector is configured to detect the acoustic signal emitted by the acoustic source.

12. The downhole tool of claim 11 further comprising an intermediate section of the housing coupling the first and second sections, wherein a fluid sample area of the intermediate section is open to fluid from the borehole, and wherein the fluid sample area is positioned within the intermediate section to allow the fluid to pass through the acoustic signal between the acoustic source and the acoustic detector.

13. The downhole tool of claim 9 wherein the downhole tool is configured for conveyance in a wellbore via at least one of a wireline and a drill pipe.

\* \* \* \* \*